United States Patent [19]

Debono

[11] 4,322,343

[45] Mar. 30, 1982

[54] PSEUDO-AGLYCONE OF ACTAPLANIN

[75] Inventor: Manuel Debono, Indianapolis, Ind.

[73] Assignee: Eli Lilly and Company, Indianapolis, Ind.

[21] Appl. No.: 217,961

[22] Filed: Dec. 18, 1980

[51] Int. Cl.$^3$ .................... C07C 103/52; A61K 35/00
[52] U.S. Cl. ............................ 260/112.5 R; 424/118
[58] Field of Search ........................... 260/8, 112.5 R; 424/118

[56] References Cited

U.S. PATENT DOCUMENTS 3,952,095 4/1976 Hamill et al. ..................... 424/118
4,064,233 12/1977 Hamill et al. ..................... 424/118
4,115,552 9/1978 Hamill et al. ..................... 424/118

*Primary Examiner*—Delbert R. Phillips
*Attorney, Agent, or Firm*—Gerald V. Dahling; Arthur R. Whale

[57] ABSTRACT

Antibiotic A-4696 pseudo-aglycone, produced by mild acid hydrolysis of the actaplanin antibiotic A-4696 complex, has antibacterial and growth promotant activity.

4 Claims, 1 Drawing Figure

PSEUDO-AGLYCONE OF ACTAPLANIN

BACKGROUND OF THE INVENTION

The present invention is related generally to the inventions disclosed in U.S. Pat. No. 3,952,095 issued Apr. 20, 1976, for novel antibiotic and a process for the production thereof, U.S. Pat. No. 4,064,233 issued Dec. 20, 1977, for antibiotic A-4696, U.S. Pat. No. 4,115,552 issued Sept. 19, 1978, for factor A and B of antibiotic A-4696, and copending U.S. application of Manuel Debono, Kurt E. Merkel, Robert E. Weeks, and Herold J. Cole, for Antibiotic A-4696 Factors $B_1$, $B_2$, $B_3$, $C_{1a}$, $C_3$, and $E_1$, Attorney Docket No. X-5366, filed concurrently herewith at even date.

An aglycone hydrolysis derivative of antibiotic A-4696 was described in the above cited U.S. Pat. Nos. 4,064,233 and 4,115,552 but the hydrolysis derivative was not the pseudo-aglycone of the present invention. It is possible but not certain that a minute amount (2% or less) of the pseudo-aglycone may have been produced by the hydrolysis procedure disclosed in the prior patents. However, the hydrolysis conditions as earlier described, do not favor pseudo-aglycone formation and, if any antibiotic A-4696 pseudo-aglycone was produced, it was not recognized or appreciated at the time.

SUMMARY OF THE INVENTION

The present invention relates to a novel pseudo-aglycone hydrolysis derivative of both the actaplanin antibiotic A-4696 complex and also the factors of which it is comprised. Actaplanin antibiotic A-4696 is a complex of glycopeptide antibiotics produced by *Actinoplanes missouriensis* ATCC 31683. Mild acid hydrolysis of the antibiotic A-4696 complex or the individual constituent factors results in the pseudo-aglycone of the present invention. For purposes of the present application, the constituent factors of the antibiotic A-4696 complex do not include degradation products.

The novel antibiotic A-4696 pseudo-aglycone shows antibiotic activity and is useful in the treatment of tooth decay, gum disease, and other health problems caused by pathogenic microorganisms. In addition, the antibiotic of the present invention has agricultural application as a growth promotant in chickens, swine, sheep, and beef cattle.

DETAILED DESCRIPTION OF THE INVENTION

Figure 1:
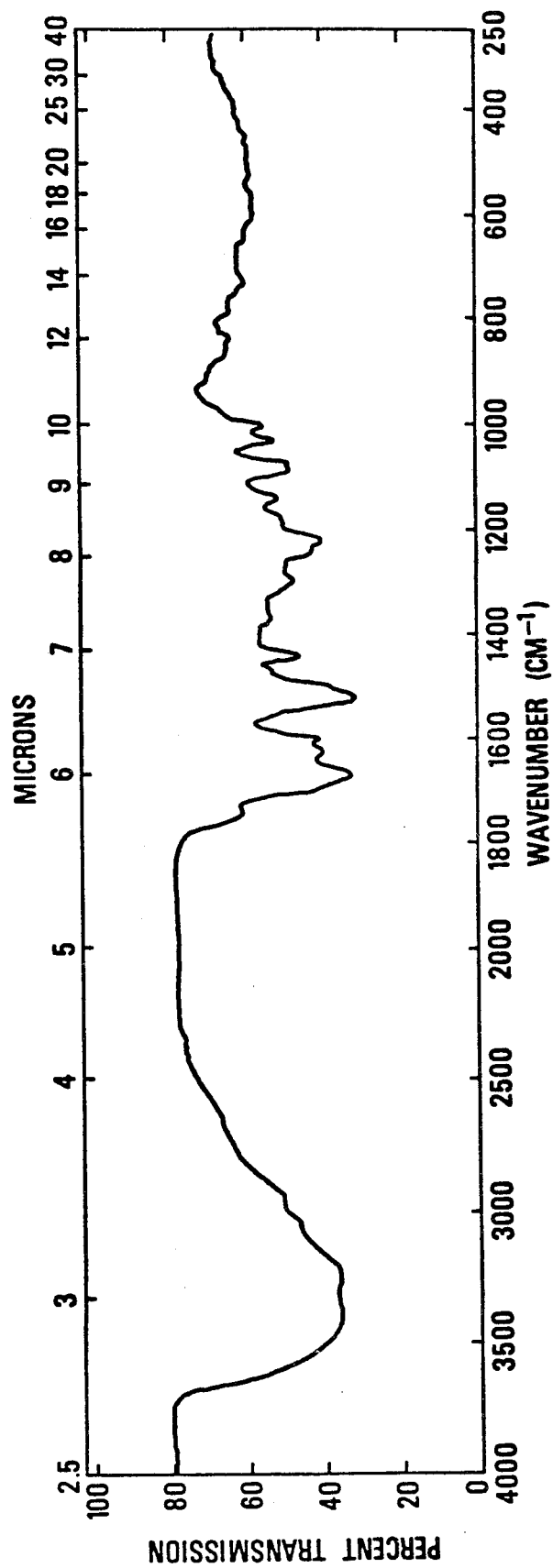

The novel antibiotic A-4696 pseudo-aglycone of the present invention is a basic compound capable of forming salts with suitable acids. For example, the antibiotic is conveniently produced from antibiotic A-4696 complex or a factor therein by mild acid hydrolysis with HCl to form the dihydrochloric acid salt. Other pharmaceutically acceptable salts can also be prepared by employing methods known in the art. The antibiotic A-4696 pseudo-aglycone is represented by the following structural formula:

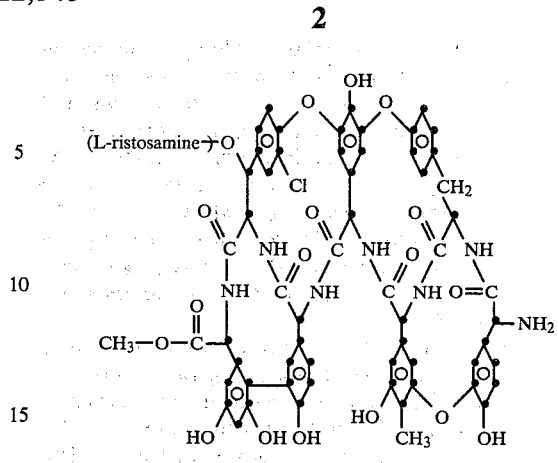

Bioautography of the products of mild hydrolysis of the antibiotic A-4696 complex shows a rapid appearance of the antibiotic A-4696 pseudo-aglycone with the concomitant disappearance of the original material. The antimicrobial spectrum of the pseudo-aglycone of the present invention is substantially identical with that of the parent complex.

Antibiotic A-4696 pseudo-aglycone, as the dihydrochloride salt, is a white crystalline compound with a charring point of about 270° C. It is soluble in water, and insoluble in solvents such as methanol, acetone, ether, chloroform, pyridine, benzene, aliphatic hydrocarbons, and the like. It is stable over a pH range of about 1.2 to about 9.5, at temperatures of about 35° to 85° C.

Elemental analysis of antibiotic A-4696 pseudo-aglycone dihydrochloride ($C_{66}H_{61}O_{20}N_8Cl.2HCl.6H_2O$) gave the following values with oxygen comprising the remainder:

| Element | Percent Theoretical | Percent Found |
| --- | --- | --- |
| Carbon | 52.75 | 52.75 |
| Hydrogen | 5.03 | 5.15 |
| Nitrogen | 7.45 | 7.82 |
| Chlorine | 7.07 | 7.17 |

The ultraviolet absorption maximum of antibiotic A-4696 pseudo-aglycone dihydrochloride in methanol is at 279 nm with an $E_{1\ cm}^{1\%}$ of 63.6.

The infrared absorption spectrum of antibiotic A-4696 pseudo-aglycone dihydrochloride in KBr is shown in FIG. 1 of the accompanying drawing. The observed distinguishable absorption maxima over the range of 4000-700 $cm^{-1}$ are as follows: 3374 broad, 3220, 1728, 1659, 1617, 1592, 1546, 1509, 1489, 1461, 1431, 1355, 1288, 1229, 1208, 1175, 1126, 1103, 1071, 1058, 1014, 986, 897, 880, 843, 816, 767, 731, 710 $cm^{-1}$.

By employing methods known in the art, pharmaceutically acceptable salts of antibiotic A-4696 pseudo-aglycone can be prepared with mineral acids such as hydrochloric, hydrobromic, sulfonic, phosphoric, and the like. The antibiotic salts of such acids can be prepared, for example, by acidifying a solution of the antibiotic free-base with the desired acid and then precipitating the salt by introducing acetone to the solution. The salts can likewise be prepared in certain instances by ion exchange on an ion exchange column. Other known methods for the preparation of antibiotic salts can also be employed.

The novel antibiotic A-4696 pseudo-aglycone has an inhibiting action on the growth of many microbial organisms which are pathogenic to man, animals and plants, and is therefore useful in suppressing the growth of such organisms. The levels at which antibiotic A-4696 pseudo-aglycone as a dihydrochloride, inhibits the growth of illustrative organisms is set forth in Table 1 below. The inhibition levels were determined by the agar-dilution test and are stated in terms of the minimum inhibitory concentration (MIC), microgram(s) per milliliter (mcg./ml.).

In the agar-dilution test the test organism is streaked or implanted on agar plates containing various concentrations of antibiotic A-4696 pseudo-aglycone dihydrochloride in the agar. The test plates are incubated at 37° C. for 48 hours, and the MIC is determined as the plate at the lowest concentration of the antibiotic where growth of the test organism is inhibited.

The results of are as follows:

TABLE 1

| Test Organism | Minimum Inh. Concentration Antibiotic A-4696 Pseudo-Aglycone (mcg./ml) |
|---|---|
| Staphylococcus aureus X1.1 | 0.25 |
| Staphylococcus aureus V41 | 0.25 |
| Staphylococcus aureus X400 | 0.5 |
| Staphylococcus aureus S13E | 0.25 |
| Staphylococcus epidermidis 1 | 0.5 |
| Staphylococcus epidermidis 2 | 0.5 |
| Streptococcus Group A C203 | 0.25 |
| Streptococcus Group D X66 | 0.50 |
| Streptococcus Group D 9960 | 0.50 |
| Streptococcus pneumoniae Park | 0.25 |
| Haemophilus influenzae sens. BRUN | 16 |
| Haemophilus influenzae res. 251 | 32 |
| Shigella sonnei N9 | 32 |
| E. coli N10 | 128 |
| E. coli 14 | 64 |
| E. coli TEM | 8 |
| Klebsiella pneumoniae X26 | 128 |
| Klebsiella pneumoniae KAE | >128 |
| Enterobacter aerogenes X68 | >128 |
| Enterobacter aerogenes C32 | >128 |
| Enterobacter aerogenes EB17 | >128 |
| Enterobacter cloacae EB5 | >128 |
| Enterobacter cloacae 265A | >128 |
| Salmonella typhosa X514 | >128 |
| Salmonella typhosa 1335 | 128 |
| Pseudomonas aeruginosa X528 | >128 |
| Pseudomonas aeroginosa X239 | >128 |
| Pseudomonas aeruginosa Ps18 | >128 |
| Serratia marcescens X99 | 32 |
| Serratia marcescens SE3 | 128 |
| Proteus morganii PR15 | 128 |
| Proteus inconstans PR33 | >128 |
| Proteus rettgeri PR7 | 32 |
| Proteus rettgeri C24 | >128 |
| Citrobacter freundii CF17 | >128 |
| Bordetella bronchiseptica 16 | 32 |

Antibiotic A-4696 pseudo-aglycone dihydrochloride, as seen from the above data, is an effective antibacterial and antimicrobial agent. Accordingly the incorporation of antibiotic A-4696 pseudo-aglycone or an acid addition salt thereof, into an appropriate toothpaste, gel, powder, or the like, or a suitable mouthwash, or other oral hygiene preparation, can provide an effective method for inhibiting the development of dental caries and periodontal disease which are associated with bacterial action. Alternatively, a solution of antibiotic A-4696 pseudo-aglycone or an acid addition salt thereof at an appropriate concentration, can be applied to the surface of the gums and teeth with a suitable swab.

Antibiotic A-4696 pseudo-aglycone also shows growth promotant activity and accelerates the growth rate and increases feed efficiency in poultry, swine, sheep, and beef cattle. For example, the daily ingestion by poultry and swine of the antibiotics of the present invention in an amount of about 0.5 mg. to about 25 mg./kg. of body weight, results in faster growth and greater feed efficiency than that registered by animals fed the same basal ration without the active agent. The term "basal ration" refers to the total feed intake of the animal, and consists of the various feedstuffs, concentrates, supplements, minerals, vitamins or medicated premixes, roughages, and the like containing the dietary requirements of the animal. Typical basal rations for poultry and swine are found in U.S. Pat. No. 4,115,552.

In an important embodiment of the present invention, antibiotic A-4696 pseudo-aglycone, or a suitable acid addition salt thereof, is administered orally in a suitable feed in an amount of about 2 to 200 grams per ton of total feed to provide for increased feed efficiency and growth promotion activity. The addition of the active antibiotic of this invention to animal feed is preferably accomplished by preparing an appropriate feed premix (such as, for example, is disclosed in U.S. Pat. No. 4,115,552) containing about 1 to 100 grams of antibiotic A-4696 pseudo-aglycone or a suitable acid addition salt thereof, per pound of premix. The completed premix is then incorporated into the final ration. Alternatively, an intermediate concentrate or feed supplement containing the active agent can be blended into the feed.

While the novel antibiotic A-4696 pseudo-aglycone is useful in several different ways, it is particularly effective as an antibiotic. Substances which exhibit this type of activity are always in demand, not only for the treatment of tooth decay and gum disease, but also for the treatment of the other microbially related health problems generally.

The novel antibiotic A-4696 pseudo-aglycone is best produced by mild acid hydrolysis of the antibiotic A-4696 complex although it can also be produced by mild acid hydrolysis of any of the factors contained therein. The antibiotic A-4696 complex can be obtained by culturing an organism of the genus Actinoplanes under aerobic conditions in a suitable culture medium until the culture medium contains substantial antibiotic activity. The antibiotic can be recovered by employing various isolation and purification procedures commonly used and understood in the art.

The microorganism used for the production of the antibiotic A-4696 complex which is useful as a starting material for production of antibiotic A-4696 pseudo-aglycone has been identified as a strain of *Actinoplanes missouriensis* of the family Actinoplanaceae. The Actinoplanaceae are a family of microorganisms of the order Actinomycetales, having been first described by Dr. John N. Couch, Jour. Elisha Mitchell Sci. Soc., 65, 315–318 (1949); and 66, 87–92 (1950); Trans. New York Acad. Sci., 16, 315–318 (1954); Jour. Elisha Mitchell Sci. Soc., 71, 148–155 and 269 (1955); Bergey's Manual of Determinative Bacteriology, 7th Edition, 825–829 (1957); and Jour. Elisha Mitchell Sci. Soc., 79, 53–70 (1963).

The *Actinoplanes missouriensis* strain useful for the production of the antibiotic A-4696 starting material has been deposited and made a part of the stock culture collection, Rockville, Maryland, from which it is available to the public without restriction under the number ATCC 31683.

*Actinoplanes missouriensis* strains ATCC 31683 is characterized by the physical and cultural properties set forth in the following paragraphs.

The strain is derived by a series of mutations from ATCC 23342 which was previously disclosed in U.S. Pat. No. 4,115,552. The present strain produces a similar substrate or mycelium and the morphology is substantially indistinguishable from that of the parental strain. Neither aerial, secondary mycelia, nor sporangia are observed and moreover, techniques such as growth on pollen grains, likewise fails to yield any sporangia.

The methods used for the taxonomic studies of strain ATCC 31683 are well known to those skilled in the art and in large part are methods recommended for the International Streptomyces Project (ISP), described by Shirling and Gottlieb, 1966, Intern. J. of Systematic Bacteriol. 16(3):313–340. Enzyme assays were carried out according to the methods of Blazevic and Ederer, 1975, Principles of Biochemical Tests in Diagnostic Microbiology, John Wiley and Sons, Inc., New York, and color names, abbreviations, and numbers were assigned using the ISCC-NBS method of Kelly and Judd, 1976, The ISCC-NBS Centroid Color Charts Standard Sample No. 2106, U.S. Dept. of Commerce, National Bureau of Standards, Washington D.C. Lysozyme resistance and the decomposition of casein, esculin, hypoxanthine, tyrosine, and xanthine were measured using the procedure of Berg, 1973, Appl. Microbiol. 25:665–681. Carbon utilization studies were also completed and are scored as follows:

++ =equal to or < glucose control; positive utilization

+ = < glucose control, < no carbon control; positive utilization (+)=growth questionable; doubtful utilization − =no growth; negative utilization Accordingly a taxonomic description, including both the cultural and physiological characteristics, of the Actinoplanes strain of the present invention is given in tabular form below.

| General Culture And Physiological Characteristics of Actinoplanes Strain ATCC 31683 | |
|---|---|
| Property Observed | Characteristics |
| Culture characteristics on: | |
| ISP medium no. 2 | Growth good, reverse 90.gy.Y; no aerial mycelium; no soluble pigment. |
| ISP medium no. 3 | Growth good, reverse 93.yGray; no aerial mycelium; no soluble pigment. |
| ISP medium no. 4 | Growth good, reverse 79.1.gy.yBr; no aerial mycelium; no soluble pigment. |
| ISP medium no. 5 | Growth fair, reverse 90.gy.Y; no aerial mycelium; no soluble pigment. |
| ISP medium no. 7 | Growth fair, reverse 80.gy.yBr; no aerial mycelium; soluble pigment light brown. |
| Bennett's agar | Growth abundant, reverse 93.yGray; no aerial mycelium; no soluble pigment. |
| Calcium malate | Growth good, shiny, reverse 93.yGray; no aerial mycelium; no soluble pigment. |
| Czapek's agar | Growth abundant, reverse 93.yGray; no aerial mycelium; no soluble pigment. |
| Glucose - asparagine | Growth good, reverse 93.yGray; no aerial mycelium; no soluble pigment. |
| Tomato paste - oatmeal | Growth good, reverse 91.d.gy.Y; no aerial mycelium; no soluble pigment. |
| Anio - Hensen's agar | Growth fair, reverse 91.d.gy.Y; no aerial mycelium; no soluble pigment. |
| 53H medium | Growth good, reverse 91.d.gy.Y; no aerial mycelium; no soluble pigment. |
| Czapek's peptone | Growth abundant, reverse 90.gy.Y; no aerial mycelium; no soluble pigment. |
| Casein decomposition | Positive |
| Catalase reaction | Positive |
| Esculin decomposition | Positive |
| Gelatin liquefaction | Positive (100%) |
| $H_2S$ production in ISP medium no. 6 | Trace |
| Hypoxanthine decomposition | Negative |
| Lysozyme resistance | Negative |
| Melanoid pigments on | |
| ISP medium no. 1 | Negative |
| ISP medium no. 6 | Negative |
| ISP medium no. 7 | Negative |
| ISP medium no. 7 minus tyrosine | Negative |
| NaCl tolerance on ISP medium no. 2 | <2% |
| Nitrate reduction | Negative |
| pH growth range on ISP medium no. 2 | 6–8.4 |
| Phosphatase production | Positive |
| Skim milk reaction | Negative |
| Starch hydrolysis on ISP medium no. 4 | Negative |
| Sucrose tolerance on ISP medium no. 2 | 20% |
| Temperature growth range on ISP medium no. 2 | 5–40° C. |
| Tyrosine decomposition | Positive |
| Urease production | Negative |
| Antibiotic sensitivity: | |
| Cephalothin (sodium) 30 μg. | Sensitive |
| Erythromycin (estolate) 15 μg. | Sensitive |
| Chloromycetin 30 μg. | Sensitive |
| Novobiocin 30 μg. | Sensitive |
| Penicillin (G) 10 units | Sensitive |
| Rifampin 5 μg. | Sensitive |
| Streptomycin 10 μg. | Sensitive |
| Tetracycline 30 μg. | Sensitive |
| Vancomycin HCl 30 μg. | Sensitive |
| Xanthine production | Negative |
| Carbon utilization on ISP medium no. 9* with: | |
| no carbon | − |
| glucose | ++ |
| L-arabinose | ++ |
| cellobiose | ++ |
| D-fructose | ++ |
| D-galactose | ++ |
| i-inositol | − |
| D-mannitol | ++ |
| melibiose | + |
| raffinose | + |
| D-rhamnose | + |
| D-ribose | + |
| salicin | + |
| sucrose | + |
| D-xylose | ++ |

*Sterilized carbon sources were added to equal a final concentration of 1.0%.

The *Actinoplanes missouriensis* strain ATCC 31683 can be grown in any one of a number of different culture media. However for economy in production, maximum yield, and ease of isolation of the antibiotic starting material, certain culture media are preferred. Thus, for example, starch is one of the preferred sources of carbohydrate, and yeast is one of the preferred nitrogen sources. Other carbohydrate sources which can be used include molasses, glucose, dextrin, glycerol, and the like. Nitrogen sources also include amino acid mixtures, peptones, and the like.

Nutrient inorganic salts to be incorporated in the culture media can include the customary salts capable of yielding sodium, potassium, ammonia, calcium, phosphate, chloride, sulfate, and like ions. Additionally, sources of growth factors, such as distillers' solubles and yeast extracts, can be included with beneficial effect on the production of antibiotic A-4696.

As is necessary for the growth and development of other microorganisms, essential trace elements should also be included in the culture medium for growing the Actinoplanes sp. employed in this invention. Such trace elements are commonly supplied as impurities incidental to the addition of the other constituents of the medium.

The organism used to produce antibiotic A-4696 for production of the pseudo-aglycone can be grown over a relatively wide pH range. However it is desirable to culture the organism in a medium with a pH between about 6.5 and 7.0. As with other Actinomycetes, the pH of the growing medium gradually changes during the growth period; the pH at the end of the fermentation period usually ranging from about 6.5 to 7.5.

Submerged aerobic cultural conditions are preferred for the production of the antibiotic A-4696 starting material. Relatively small amounts of the antibiotic can be produced by shake flask culture; however, for the preparation of large amounts, submerged aerobic culture in sterile tanks is preferred. The culture medium in the sterile tank can be inoculated with a mycelial fragment suspension.

Accordingly, it is desirable to produce a vegetative inoculum of the organism by inoculating a relatively small quantity of culture medium with the mycelial fragments of the organism, and when a young active vegetative inoculum is obtained, to aseptically transfer it to the large tank. The medium in which the vegetative inoculum is grown can be the same as that utilized for large scale production although other media can be employed.

*Actinoplanes missouriensis* strain ATCC 31683 grows at temperatures between 20° and 40° C. although the largest amounts of the antibiotic A-4696 starting material appear to be produced at a temperature of about 30° C.

Sterile air is blown through the culture medium in the submerged aerobic culture process. The volume of air sparged into the culture medium varies from about 0.1 to about 1.0 volume of air per minute per volume of culture medium. The most efficient growth and antibiotic production are achieved when the volume of air is at least ½ volume of air per minute per volume of culture medium.

The rate of production and the concentration of antibiotic activity in the culture medium can be followed during the growth period by testing samples of the fermentation broth for antibiotic activity against organisms known to be susceptible to the antibiotic. One such useful assay organism is *Bacillus subtilis*. The bioassay can be carried out by the standard cup-plate method, or by the paper disc assay on agar plates.

Generally, maximum production of the antibiotic occurs within about 4 to 6 days in shake flasks or submerged aerobic culture fermentations.

Antibiotic A-4696 useful as starting material for production of antibiotic A-4696 pseudo-aglycone can be recovered from the culture medium and separated from other substances which may be present by adsorptive and extractive techniques. Adsorptive techniques are preferred because such procedures avoid the use of large volumes of solvents required in extraction processes.

The antibiotic A-4696 pseudo-aglycone of the present invention is further illustrated by the following examples:

EXAMPLE 1

Preparation of Antibiotic A-4696 Complex and Individual Factors as Starting Material For Antibiotic A-4696 Pseudo-Aglycone

A. Shake Flask Fermentation

Mycelial fragments of *Actinoplanes missouriensis* strain ATCC 31683 were inoculated on a nutrient agar slant having the following composition:

| Ingredient | Amount |
| --- | --- |
| Cerelose | 0.5% |
| Potato dextrin | 2.0% |
| Nutrisoy flour | 1.5% |
| Yeast extract | 0.25% |
| $CaCO_3$ | 0.1% |
| Agar | 2.0% |

The slant inoculated with ATCC 31683 was then incubated for 6 days at 30° C. The culture does not sporulate so it is necessary to macerate the mycelial mat with a sterile pipette. The macerated mature culture was covered with sterile distilled water and scraped carefully with the pipette or a sterile rod to obtain a mycelial suspension.

The suspension thus obtained was used to inoculate 100 ml. of a sterile vegetative medium having the following composition:

| Ingredient | Amount |
| --- | --- |
| Cerelose | 0.5% |
| Potato dextrin | 2.0% |
| *Nutrisoy flour | 1.5% |
| Yeast extract | 0.25% |
| $CaCO_3$ | 0.1% |

*Nutrisoy fluor is obtained from Archer Daniels Midland Company, 4666 Faries Parkway, Decatur, Illinois 62526.

The inoculated vegetative medium was grown for 48 hours at 30° C. on a rotary shaker operating at 250 rpm. Ten ml. of the inoculated vegetative medium was inoculated into 100 ml. of a sterile "bump" medium of the following composition.

| Ingredient | Amount |
| --- | --- |
| Cerelose | 0.5% |
| Yeast | 0.25% |
| Nutrisoy flour | 1.5% |
| Corn starch | 2.0% |
| $CaCO_3$ | 0.1% |

-continued

| Ingredient | Amount |
|---|---|
| *Sag 471 | 0.05% |

*Sag 471 is a well known silicone antifoaming agent available from Union Carbide Company, 120 Riverside Plaza, Chicago, Illinois 60606.

The inoculated "bump" medium was incubated for 24 hours at 30° C. with constant shaking on a rotary shaker operating at 250 rpm.

Four-tenths ml. of the "bump" medium was inoculated into 100 ml. portions of a production medium of the composition shown below contained in 500 ml. Erlenmeyer flasks, and sterilized at 121° C. for 30 minutes.

| Ingredient | Amount |
|---|---|
| Cerelose | 1.25% |
| Corn starch | 4.4% |
| Sucrose | 3.75% |
| Molasses | 2.0% |
| Yeast | 1.25% |
| *Proflo (Cotton seed flour) | 1.25% |
| $CaCO_3$ | 0.25% |
| $K_2HPO_4$ | 0.625% |
| $(NH_4)_2SO_4$ | 0.031% |
| Sag 471 | 0.03% |

*Proflo is obtained from Traders Protein Division, Traders Oil Mill Company, P.O. Box 1837, Fort Worth, Texas 76101.

The production fermentation was shaken for about 96 hours at a temperature of 30° C. on a rotary shaker operating at 250 rpm. The pH at the end of the fermentation cycle was about 8.0.

B. 40-Liter Tank Fermentation

The preparation of the inoculum proceeded through the incubation of the "bump" medium detailed under section A, above. Twenty-five liters of a production medium as outlined above, was sterilized by autoclaving at 121° C. for 30 minutes and charged into a 40 l. fermentation tank. One-hundred ml. of inoculated "bump" medium was inoculated into the sterile production medium. The inoculated production medium was allowed to ferment for 4 days at 30° C. The fermentation was aerated with sterile air in an amount of about one-half volume of air per volume of culture medium per minute. The fermenting production medium was agitated with a mixer utilizing an impeller of a proper size and turning at an appropriate rpm to insure adequate mixing of air with the medium. The pH of the culture medium gradually increased from an initial level of about 6.5 to about 8.0 as the fermentation proceeded.

C. Isolation of Antibiotic A-4696 Complex

The fermentation broth (3800 l.) prepared according to the above teaching was filtered after the addition of 5% (wt/vol) filter aid (Celite 545). The filter cake was resuspended in deionized water (3600 l.) and the pH of the aqueous suspension was adjusted to pH 10.5 using aqueous sodium hydroxide. The suspended solids were separated by filtration and washed with water. The filtrate and the washings were combined and the resulting solution was acidified with 20% (wt/vol) aqueous sulfuric acid to pH 4.5. The acidic solution was clarified by filtration using 1% filter aid (Celite 545). The clear solution was passed through a column (1.8×5 ft.) containing 350 l. of Amberlite IR-116 (Na+ form) and the column washed with deionized water (1200 l.). The IR-116 resin was removed from the column and eluted batchwise at pH 10.5 with an aqueous solution of sodium hydroxide (total 1000 liters). The resin eluate was neutralized (pH 7) with 20% (wt/vol) aqueous sulfuric acid, then washed with three portions of deionized water (150 liters total). The water washes were neutralized and combined with the neutralized eluate. The resulting solution was concentrated and subsequently freeze dried. The preparation of the crude complex varied in color from tan to dark brown.

D. Removal of Salts from Crude Antibiotic A-4696 Complex

The crude complex (1.0 kg) was slowly added with vigorous stirring to deionized water (1.5 liters). The resulting suspension was stirred for twenty minutes and was subsequently neutralized (pH 7) using a 10% aqueous ammonium hydroxide solution. The insoluble antibiotic A-4696 complex was separated by vacuum filtration, washed with deionized water, and freeze dried. The dried, desalted complex was recovered in approximately 80% yield (based on bioactivity).

E. Purification of Desalted Antibiotic A-4696 Complex

The dried, desalted complex (300 g.) was suspended in deionized water (2 liters), and the pH of the suspension was adjusted to pH 2.7 by addition of 3 N aqueous hydrochloric acid. The acidified solution was centrifuged for 40 minutes at 2500 rpm. The supernatant was decanted and loaded on a column (8×85 cm) containing 6 liters of decolorizing resin (Duolite S761). The activity was eluted with deionized water at a flow rate of 30 ml/min. The elution was monitored by thin layer chromatography. The antibiotic A-4696-containing effluent was concentrated (3 mm., 35° C.) to a volume of 3 liters and freeze dried. The decolorized complex was recovered as a white-to-tan solid in approximately 70% yield (based on bioactivity).

F. Isolation of Individual Antibiotic A-4696 Factors

The dried, decolorized antibiotic A-4696 complex (10 g.) was dissolved in about 100 ml. distilled water. The resulting aqueous solution was filtered and separated by column chromatography using reversed phase adsorbents such as, for example, Li Chroprep[R] RP-18* as the stationary phase and aqueous acetonitrile gradients containing triethylaminephosphate as the mobile phase. Although it is understood that those skilled in the art will vary the acetonitrile concentration gradient depending upon the composition of a particular fermentation, a preferred concentration gradient is 10-40%. The column effluent was monitored by UV-activity and fractions containing the individual factors were collected. The acetonitrile was removed by evaporation under high vacuum and the resulting aqueous solutions were freeze dried. The freeze dried chromatography fractions were then redissolved in distilled water, adsorbed on reversed phase adsorbents such as, for example, Sep Pak[R] C18 cartridges** and eluted with aqueous methanol. The aqueous solutions containing the individual antibiotic A-4696 components are evaporated to dryness and the purified antibiotic A-4696 factors are then recovered as dry amorphous solids.

*Available from E. Merck, Darinstadt, Germany.
**Available from Waters Associates Inc., Milford, Massachusetts

EXAMPLE 2

Preparation of Antibiotic A-4696 Pseudo-Aglycone Dihydrochloride Salt

Antibiotic A-4696 complex (2.0 g prepared according to the teaching of Example 1 A-E) was dissolved in 50 ml. of 5% methanolic HCl and refluxed for 70 minutes. The reaction mixture was evaporated to dryness at 35°–40° C. under reduced pressure. The residue was diluted with a small amount of water which resulted in the formation of a solid which was isolated by filtration. The solid was air dried, dissolved in a small amount of methanol and reprecipitated by the addition of acetonitrile until a granular solid formed. The desired product was then filtered, dried, and was shown by high performance liquid chromatography (HPLC) to be a single homogeneous product. The identity and structure of the desired product were confirmed by plasma desorption mass spectroscopy, proton nuclear mass resonance, and elemental analysis.

Antibiotic A-4696 pseudo-aglycone dihydrochloride salt is also prepared by the mild acid hydrolysis of an individual or a mixture of constituent factors contained in the antibiotic A-4696 complex. The isolation of the various individual antibiotic A-4696 factors useful as starting material for subsequent production of antibiotic A-4696 pseudo-aglycone is taught in copending U.S. application of Manuel Debono, Kurt E. Merkel, Robert E. Weeks, and Herold J. Cole, for Antibiotic A-4696 Factors $B_1$, $B_2$, $B_3$, $C_{1a}$, $C_3$, and $E_1$, Attorney Docket No. X-5366, filed concurrently herewith at even date. An alternate separation and isolation procedure is also disclosed in Example 1F herein. The preparation of antibiotic A-4696 pseudo-aglycone dihydrochloride salt from an individual or a mixture of several constituent factors contained in the antibiotic A-4696 complex is substantially the same as the preparation of the pseudo-aglycone directly from the antibiotic A-4696 complex as described above.

The identity of the desired product prepared from an individual or a mixture of antibiotic A-4696 factors was confirmed by plasma desorption mass spectroscopy, proton nuclear mass resonance, and elemental analysis.

EXAMPLE 3

Preparation of Antibiotic A-4696 Pseudo-Aglycone Sulfate Salt

Antibiotic A-4696 complex (2.0 g. prepared according to the teaching of Example 1 A-E) was dissolved in 50 ml. of 5% methanolic sulfuric acid and refluxed for 70 minutes. The residue was diluted with a small amount of water which resulted in the formation of a solid which was isolated by filtration. The solid was air dried, dissolved in a small amount of methanol and reprecipitated by the addition of acetonitrile until a granular solid formed. The desired product was then filtered, dried, and was shown by high performance liquid chromatography (HPLC) to be a single homogeneous product. The identity and structure of the desired product were confirmed by plasma desorption mass spectroscopy, proton nuclear mass resonance, and elemental analysis.

Antibiotic A-4696 pseudo-aglycone sulfate salt is also prepared by the mild acid hydrolysis of an individual or a mixture of constituent factors contained in the antibiotic A-4696 complex. Separation of the various individual antibiotic A-4696 factors useful as starting material for subsequent production of antibiotic A-4696 pseudo-aglycone is taught in Examples 1F and 2. The preparation of antibiotic A-4696 pseudo-aglycone sulfate salt from an individual or a mixture of several constituent factors contained in the antibiotic 4696 complex is substantially the same as the preparation of the pseudo-aglycone directly from the antibiotic A-4696 complex as described above.

The identity of the desired product prepared from an individual or a mixture of antibiotic A-4696 factors was confirmed by plasma desorption mass spectroscopy, proton nuclear mass resonance, and elemental analysis.

I claim:

1. Antibiotic A-4696 pseudo-aglycone of the formula

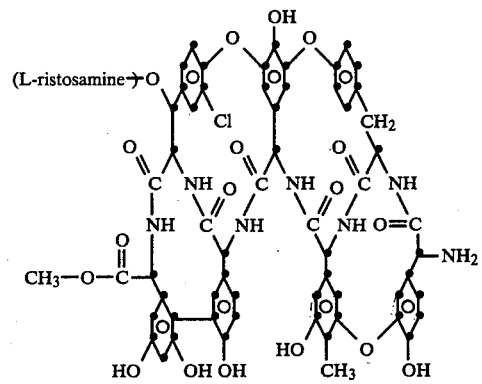

or a pharmaceutically effective inorganic acid addition salt thereof.

2. The antibiotic A-4696 pseudo-aglycone of claim 1 wherein the acid addition salt is a dihydrochloride.

3. The antibiotic A-4696 pseudo-aglycone of claim 1 wherein the acid addition salt is a sulfate.

4. The method of preparing the antibiotic of claim 1 which comprises the mild acid hydrolysis of the antibiotic A-4696 complex or a constituent factor therein.

* * * * *